United States Patent [19]

Teach

[11] Patent Number: 4,824,468
[45] Date of Patent: Apr. 25, 1989

[54] HERBICIDAL OXAZOLIDINES AND METHODS OF USE

[75] Inventor: Eugene G. Teach, El Cerrito, Calif.

[73] Assignee: ICI Americas Inc., Wilmington, Del.

[21] Appl. No.: 107,196

[22] Filed: Oct. 13, 1987

[51] Int. Cl.$^4$ .................. A01N 43/76; C07D 263/06
[52] U.S. Cl. ........................................ 71/88; 548/215
[58] Field of Search ............................ 548/215; 71/88

[56] References Cited

U.S. PATENT DOCUMENTS

| | | | |
|---|---|---|---|
| 3,707,541 | 12/1972 | Lajiness | 548/215 |
| 3,720,683 | 3/1973 | Breuer | 548/180 |
| 3,884,671 | 5/1975 | Albright | 548/215 |
| 3,959,304 | 5/1976 | Teach | 548/215 |
| 3,989,503 | 11/1976 | Pallos | 71/88 |
| 4,072,688 | 2/1978 | Teach | 548/215 |
| 4,124,372 | 11/1978 | Pallos | 71/88 |
| 4,186,130 | 1/1980 | Teach | 548/215 |
| 4,197,110 | 4/1980 | Szabo | 548/215 |
| 4,219,655 | 8/1980 | Teach | 548/215 |
| 4,236,011 | 11/1980 | Teach | 548/215 |
| 4,243,811 | 1/1981 | Teach | 548/215 |
| 4,249,931 | 2/1981 | Teach | 71/88 |
| 4,249,932 | 2/1981 | Teach | 71/88 |
| 4,268,677 | 5/1981 | Teach | 548/215 |
| 4,319,031 | 3/1982 | Teach | 548/215 |
| 4,322,240 | 3/1982 | Teach | 71/88 |
| 4,350,517 | 9/1982 | Teach | 548/215 |
| 4,400,200 | 8/1983 | Teach | 71/88 |
| 4,723,986 | 2/1988 | Teach | 548/215 |

FOREIGN PATENT DOCUMENTS 2033282 1/1971 Fed. Rep. of Germany ...... 548/215

Primary Examiner—Donald G. Daus
Assistant Examiner—Mark W. Noel
Attorney, Agent, or Firm—Denis A. Polyn

[57] ABSTRACT

An oxazolidine having the formula

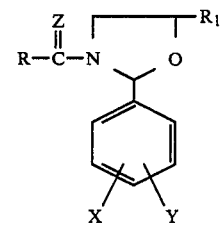

wherein R is selected from the group consisting of alkyl, substituted alkyl, alkenyl, cycloalkyl, benzyl, alkoxyalkyl, carboalkoxyalkyl, alkylthioalkyl, phenyl, substituted phenyl, furanyl, phenoxyalkyl, carboalkoxy, substituted phenoxyalkyl, alkylamino, alkoxy, chloroethylamino, alkylthio, cycloalkylalkyl, cycloalkenylalkyl, phenylamino, substituted phenylamino, alkenylamino, and benzylamino; Z is selected from the group consisting of oxygen or sulfur; $R_1$ is selected from the group consisting of alkyl or halosubstituted alkyl wherein the alkyl group has from 1 to 4 carbon atoms; and X and Y are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups in each alkyl-containing moiety have from 1 to 4 carbon atoms. Also disclosed is a method of use.

30 Claims, No Drawings

HERBICIDAL OXAZOLIDINES AND METHODS OF USE

BACKGROUND OF THE INVENTION

The present invention relates to certain oxazolidine compounds which are useful as pre-emergent and post-emergent herbicides against grasses and broadleaf weed species.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

The oxazolidine compounds of this invention are not known in the art. Oxazolidine compounds, however, of somewhat similar structures are known in the art. These compounds are disclosed and claimed in a number of patents, including U.S. Pat. No. 4,400,200, U.S. Pat. No. 4,322,240; German Offen. No. DE 2,605,586, European Pat. No. EP 21759 and French Pat. No. 1,560,931.

As described in the U.S. and German patents, the oxazolidine compounds therein are effective as antidotes to protect crop plants from injury due to various herbicides.

In contrast, the oxazolidine compounds of this invention in themselves exhibit excellent herbicidal activity.

DESCRIPTION OF THE INVENTION

It has now been discovered that certain new and novel oxazolidines have good herbicidal and plant growth regulating activity, particularly when applied as pre- or post-emergent herbicides and used against grasses or broadleaf weed species.

As used herein, the term "herbicide" means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing and the like.

The new and novel compounds of this invention have the formula

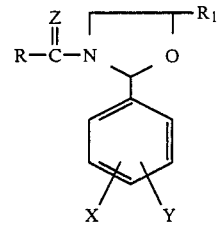

wherein
R is selected from the group consisting of alkyl having from 1 to about 8 carbon atoms, substituted alkyl wherein the alkyl group has from 1 to about 8 carbon atoms and the substituent is selected from the group consisting of halogen or trifluoromethyl, alkenyl having from 2 to about 5 carbon atoms, cycloalkyl in which the cyclo ring has from 3 to about 6 carbon atoms and the alkyl group has from 1 to about 3 carbon atoms, benzyl, alkoxyalkyl wherein the alkoxy group has from 1 to about 2 carbon atoms and the alkyl group has from 1 to about 2 carbon atoms, carboalkoxyalkyl wherein the alkoxy group has from 1 to about 2 carbon atoms and the alkyl group has from 1 to about 5 carbon atoms, alkylthioalkyl wherein the alkylthio group has from 1 to about 3 carbon atoms and the alkyl group has from 1 to about 3 carbon atoms, phenyl, substituted phenyl wherein the substituent is selected from the group consisting of halogen or trifluoromethyl, furanyl, phenoxyalkyl wherein the alkyl group has from about 1 to about 2 carbon atoms, carboalkoxy wherein the alkoxy group has from 1 to about 3 carbon atoms, substituted phenoxyalkyl wherein the alkyl group has from 1 to about 2 carbon atoms and the substituent is selected from the group consisting of halogen and trifluoromethyl, alkylamino wherein the alkyl group has from 1 to about 6 carbon atoms, alkoxy having from from 1 to about 5 carbon atoms, chloroethylamino, alkylthio wherein the alkyl group has from 1 to about 5 carbon atoms, cycloalkylalkyl wherein the cyclo ring has from 3 to about 6 carbon atoms and each alkyl group has from 1 to about 3 carbon atoms, cycloalkenylalkyl wherein the cyclo ring has from 5 to about 6 carbon atoms and each alkyl group has from 1 to about 3 carbon atoms, phenylamino, substituted phenylamino wherein the substituent is selected from the group consisting of halogen, trifluoromethyl or cyano, alkenylamino wherein the alkyl group has from 2 to about 5 carbon atoms, and benzylamino;

Z is selected from the group consisting of oxygen or sulfur;

$R_1$ is selected from the group consisting of alkyl or halo-substituted alkyl wherein the alkyl group has from 1 to 4 carbon atoms; and X and Y are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups in each alkyl-containing moiety have from 1 to 4 carbon atoms.

The oxazolidine compounds of this invention can be made by reacting an appropriate benzaldehyde with an amino alcohol to produce an intermediate oxazolidine, then reacting the intermediate with an appropriate acylating or other compound to produce the desired end product. The benzaldehyde starting compounds are commercially available. The amino alcohols can be made by reacting an epoxy alkane with ammonia, as indicated in Example I below.

EXAMPLE 1

1-Amino-2-butanol

Three moles, 216 g, of 1,2-epoxybutane was added dropwise to 2100 ml of concentrated ammonia cooled in an ice-bath. The mixture was allowed to stand in the hood overnight at ambient temperature. The reaction mixture was combined with two similar reactions and the water and ammonia were stripped under vacuum. Distillation of the residue gave 306 g of the title compound, b.p. 41°–43° C. at 0.35–0.6 mm.

Example 2 below illustrates the preparation of one of the intermediate oxazolidines.

EXAMPLE 2

2-(m-Chlorophenyl)-5-ethyl-1,3-oxazolidine

Twenty-five grams of m-chlorobenzaldehyde was combined with 15.8 g of 1-amino-2-butanol and heated on the rotary evaporator for 1 hour to remove water. The yield was 37.9 g, $n_D^{30}$ 1.5741.

Other oxazolidine intermediates were made similarly.

The overall reaction for the preparation of the oxazolidines of this invention, beginning with the amino alcohol and benzaldehyde starting materials, can be represented as follows.

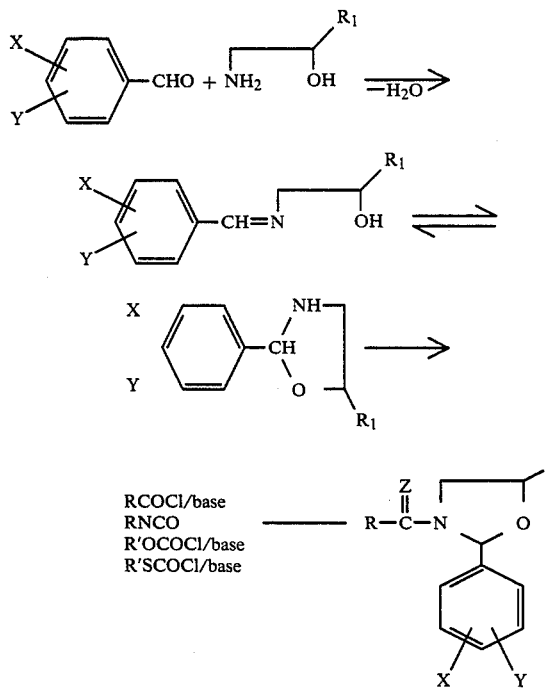

wherein X, Y, R, $R_1$ and Z are as previously defined.

Examples 3–12 below illustrate the preparation of representative ones of these compounds.

EXAMPLE 3

2-(m-Trifluoromethylphenyl)-3-S-ethylthiocarbamyl-5-ethyl-1,5-oxazolidine

Four and four-tenths grams of 2-(m-trifluoromethylphenyl)-5-ethyl-1,3-oxazolidine was combined with 2 g of triethylamine in 50 ml of benzene in an ice-bath and 2.3 g of ethyl chlorothioformate was added dropwise with stirring. When addition was complete the mixture was warmed to room temperature, washed with 1M NaOH, 1M HCl and water. The solvent was dried over anhydrous MgSO₄ and stripped on the rotary evaporator. Yield was 4 g, $n_D^{30}$ 1.5214. The structure was confirmed by NMR and infrared spectroscopy.

EXAMPLE 4

2-(m-chlorophenyl)-3-isovaleroyl-5-ethyl-1,3-oxazolidine

Four and two-tenths grams of 2-(m-chlorophenyl)-5-ethyl-1,3-oxazolidine was combined with 1.7 g of pyridine in 25 ml of methylene chloride and 2.4 g of isovaleroyl chloride was added dropwise with stirring and the mixture was stirred overnight. The mixture was washed with 50 ml of 5% NaOH and 200 ml of water, dried with MgSO₄ and stripped under vacuum. The yield was 2.4 g, $n_D^{30}$ 1.5490. The structure was confirmed by NMR and infrared spectroscopy.

EXAMPLE 5

2-(m-Trifluoromethylphenyl)-3-butyroyl-5-ethyl-1,3-oxazolidine

Four and seven-tenths grams of 2-(m-trifluoromethylphenyl)-5-ethyl-1,3-oxazolidine was combined with 1.6 g of pyridine in 25 ml of methylene chloride and 2.0 g of butyroyl chloride was added dropwise. The mixture was allowed to stir overnight. The mixture was washed with 50 ml of 5% NaOH and 200 ml of water, dried and stripped on the rotary evaporator. Yield was 6.3 g, $n_D^{30}$ 1.5015. The structure was confirmed by NMR and infrared spectroscopy.

EXAMPLE 6

2-(m-Trifluoromethylphenyl)-3-isopropylcarbamyl-5-ethyl-1,3-oxazolidine

Four and four-tenths grams of 2-(m-trifluoromethylphenyl)-5-ethyl-1,3-oxazolidine was dissolved in dry acetone and 1.8 ml of isopropyl isocyanate was added dropwise. The mixture was heated at reflux for two hours, cooled and stripped on the rotary evaporator. Yield was 5.9 g of a thick, sticky gum. The structure was confirmed by NMR and infrared spectroscopy.

EXAMPLE 7

2-(m-Trifluoromethylphenyl)-3-isovaleroyl-5-ethyl-1,3-oxazolidine

Four and four-tenths grams of 2-(trifluoromethylphenyl)-5-ethyl-1,3-oxazolidine was combined with 1.5 g of pyridine in 25 ml of methylene chloride cooled in a water-bath. To this was added 2.2 ml of isovaleroyl chloride with stirring and the mixture was allowed to stir at room temperature overnight. The reaction mixture was washed with 50 ml of 5% NaOH and 200 ml of water, separated, dried over anhydrous MgSO₄ and stripped on the rotary evaporator. The yield was 4.3 g of product, $n_D^{30}$ 1.4970. The structure was confirmed by NMR and infrared spectroscopy.

EXAMPLE 8

A2-(3-trifluoromethyl-4-chlorophenyl)-3-isovaleroyl-5-ethyl-1,3-oxazolidine

Four grams of 2-(3-trifluoromethyl-4-chlorophenyl)-5-ethyl-1,3-oxazolidine was combined with 1.2 g of pyridine in 25 ml of methylene chloride and 1.7 g of isovaleroyl chloride in 10 ml of methylene chloride was added while the mixture was stirred in a water-bath. The mixture was allowed to stir overnight and then washed with 50 ml of 5% NaOH and 200 ml of water, dried over anhydrous MgSO$_4$ and stripped on the rotary evaporator. The yield was 3.8 g. The structure was confirmed by NMR and infrared spectroscopy.

EXAMPLE 9

2-(m-Cyanophenyl)-3-isovaleroyl-5-ethyl-1,3-oxazolidine

Two and five-tenths grams of isovaleroyl chloride in 10 ml of methylene chloride was added dropwise to 6.5 g of 2-(m-cyanophenyl)-5-ethyl-1,3-oxazolidine in 25 ml of methylene chloride containing 1.9 g of pyridine. The mixture was allowed to stir overnight, washed with 50 ml of 5% NaOH and 200 ml of water, dried over anhydrous MgSO$_4$ and stripped on the rotary evaporator. The yield was 3.7 g, $n_D^{30}$ 1.5455. The structure was confirmed by NMR and infrared spectroscopy.

EXAMPLE 10

2-(m-Trifluoromethylphenyl)-3-isopropylcarbonyl-5-ethyl-1,3-oxazolidine

Four and four-tenths grams of 2-(m-trifluoromethylphenyl)-5-ethyl-1,3-oxazolidine was combined with 1.5 g of pyridine in 25 ml of methylene chloride and 2.1 ml of isopropyl chloroformate in 10 ml of methylene chloride was added with stirring. The mixture was left to stir overnight. It was worked up with 50 ml of 5% NaOH and 200 ml of water, dried with anhydrous MgSO$_4$ and stripped under vacuum on the rotary evaporator. The structure was confirmed by NMR and infrared spectroscopy.

EXAMPLE 11

2-(3-Trifluoromethyl-4-chlorophenyl)-3-isopropylcarbamyl-5-ethyl-1,3-oxazolidine Four and six-tenths grams of 2-(3-trifluoromethyl-4-chlorophenyl)-5-ethyl-1,3-oxazolidine was combined with 1.5 g of isopropyl isocyanate in 25 ml of anhydrous acetone and allowed to stand overnight protected form moisture. The mixture was stripped on the rotary evaporator giving a gum. The structure was confirmed by NMR and infrared spectroscopy.

EXAMPLE 12

2-(m-Trifluoromethylphenyl)-3-(3-trifluoromethylbutyroyl)-5-ethyl-1,3-oxazolidine Three and eight-tenths grams of 2-(m-trifluoromethylphenyl)-5-ethyl-1,3-oxazolidine was combined with 1.3 g of pyridine in 25 ml of methylene chloride and 2.7 g of 3-trifluoromethylbutyroyl chloride in 10 ml of methylene chloride was added dropwise with stirring. The mixture was allowed to stand overnight and was stand overnight and was worked up with 50 ml of 5% NaOH and 200 ml of water. The mixture was dried and stripped under vacuum on the rotary evaporator. The structure was confirmed by NMR and infrared spectroscopy.

The foregoing and other compounds of the invention prepared in accordance with the processes set forth in Examples 3–12 are listed in Table I below.

TABLE I

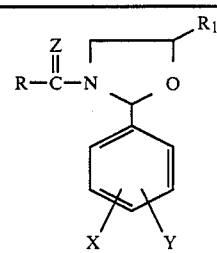

| Compound Number | R | Z | R$_1$ | X | Y |
|---|---|---|---|---|---|
| 1 | CH$_3$— | O | C$_2$H$_5$ | m-CF$_3$ | H |
| 2 | C$_2$H$_5$— | O | C$_2$H$_5$ | m-CF$_3$ | H |
| 3 | C$_3$H$_7$— | O | C$_2$H$_5$ | m-CF$_3$ | H |
| 4 | i-C$_3$H$_7$— | O | C$_2$H$_5$ | m-CF$_3$ | H |
| 5 | i-C$_4$H$_9$— | O | C$_2$H$_5$ | m-CF$_3$ | H |
| 6 | t-C$_4$H$_9$CH$_2$— | O | C$_2$H$_5$ | m-CF$_3$ | H |
| 7 | t-C$_4$H$_9$— | O | C$_2$H$_5$ | m-CF$_3$ | H |
| 8 | CH$_2$Cl— | O | C$_2$H$_5$ | m-CF$_3$ | H |
| 9 | CHCl$_2$— | O | C$_2$H$_5$ | m-CF$_3$ | H |
| 10 | CCl$_3$— | O | C$_2$H$_5$ | m-CF$_3$ | H |
| 11 | C$_4$H$_9$— | O | C$_2$H$_5$ | m-CF$_3$ | H |
| 12 | CH$_2$=CH— | O | C$_2$H$_5$ | m-CF$_3$ | H |
| 13 | c-C$_3$H$_5$— | O | C$_2$H$_5$ | m-CF$_3$ | H |
| 14 | ClCH$_2$CH$_2$— | O | C$_2$H$_5$ | m-CF$_3$ | H |
| 15 | CH$_3$CHCl— | O | C$_2$H$_5$ | m-CF$_3$ | H |
| 16 | ClCH$_2$CH$_2$CH$_2$— | O | C$_2$H$_5$ | m-CF$_3$ | H |
| 17 | CH$_2$ClCHCl— | O | C$_2$H$_5$ | m-CF$_3$ | H |
| 18 | BrCH$_2$(CH$_2$)$_4$— | O | C$_2$H$_5$ | m-CF$_3$ | H |
| 19 | ClCH$_2$(CH$_2$)$_3$— | O | C$_2$H$_5$ | m-CF$_3$ | H |
| 20 | (CH$_3$)$_2$C=CH— | O | C$_2$H$_5$ | m-CF$_3$ | H |
| 21 | CH$_3$CH=CH— | O | C$_2$H$_5$ | m-CF$_3$ | H |
| 22 | C$_5$H$_{11}$— | O | C$_2$H$_5$ | m-CF$_3$ | H |
| 23 | C$_6$H$_{13}$— | O | C$_2$H$_5$ | m-CF$_3$ | H |
| 24 | C$_9$H$_{19}$— | O | C$_2$H$_5$ | m-CF$_3$ | H |
| 25 | C$_2$H$_5$CH(CH$_3$)CH$_2$— | O | C$_2$H$_5$ | m-CF$_3$ | H |
| 26 | C$_6$H$_{11}$CH$_2$— | O | C$_2$H$_5$ | m-CF$_3$ | H |
| 27 | C$_2$H$_5$OCO— | O | C$_2$H$_5$ | m-CF$_3$ | H |
| 28 | CH$_3$OCOCH$_2$C(CH$_3$)$_2$CH$_2$— | O | C$_2$H$_5$ | m-CF$_3$ | H |
| 29 | CH$_3$C(Cl)$_2$— | O | C$_2$H$_5$ | m-CF$_3$ | H |
| 30 | BrCH$_2$CH$_2$— | O | C$_2$H$_5$ | m-CF$_3$ | H |
| 31 | (CH$_3$)$_2$CH—CH$_2$CH$_2$— | O | C$_2$H$_5$ | m-CF$_3$ | H |
| 32 | CF$_3$CH(CH$_3$)CH$_2$— | O | C$_2$H$_5$ | m-CF$_3$ | H |
| 33 | CH$_2$=CHCH$_2$CH$_2$— | O | C$_2$H$_5$ | m-CF$_3$ | H |
| 34 | trans-C$_2$H$_5$CH=CH— | O | C$_2$H$_5$ | m-CF$_3$ | H |
| 35 | CH$_3$OCH$_2$— | O | C$_2$H$_5$ | m-CF$_3$ | H |
| 36 | CH$_2$=C(CH$_3$)— | O | C$_2$H$_5$ | m-CF$_3$ | H |
| 37 | (CH$_3$)$_2$CHCH(CH$_3$)— | O | C$_2$H$_5$ | m-CF$_3$ | H |
| 38 | CH$_2$=CH—CH$_2$— | O | C$_2$H$_5$ | m-CF$_3$ | H |
| 39 | CH$_3$CH$_2$CH(CH$_3$)— | O | C$_2$H$_5$ | m-CF$_3$ | H |
| 40 | C$_3$F$_7$— | O | C$_2$H$_5$ | m-CF$_3$ | H |
| 41 | C$_6$H$_5$CH$_2$— | O | C$_2$H$_5$ | m-CF$_3$ | H |
| 42 | C$_2$H$_5$SCH$_2$— | O | C$_2$H$_5$ | m-CF$_3$ | H |
| 43 | CH$_3$CH=C(CH$_3$)— | O | C$_2$H$_5$ | m-CF$_3$ | H |
| 44 | c-C$_4$H$_7$ | O | C$_2$H$_5$ | m-CF$_3$ | H |
| 45 | m-CF$_3$C$_6$H$_4$— | O | C$_2$H$_5$ | m-CF$_3$ | H |
| 46 | CH=CH—CH=C—   L——O——⎦ | O | C$_2$H$_5$ | m-CF$_3$ | H |
| 47 | C$_6$H$_5$— | O | C$_2$H$_5$ | m-CF$_3$ | H |
| 48 | 2,4-Cl$_2$C$_6$H$_3$— | O | C$_2$H$_5$ | m-CF$_3$ | H |
| 49 | p-ClC$_6$H$_4$— | O | C$_2$H$_5$ | m-CF$_3$ | H |
| 50 | C$_6$H$_5$OCH$_2$— | O | C$_2$H$_5$ | m-CF$_3$ | H |
| 51 | p-ClC$_6$H$_4$OCH$_2$— | O | C$_2$H$_5$ | m-CF$_3$ | H |
| 52 | 2,4-Cl$_2$C$_6$H$_3$OCH$_2$— | O | C$_2$H$_5$ | m-CF$_3$ | H |
| 53 | C$_2$H$_5$— | O | CH$_3$ | m-CF$_3$ | H |
| 54 | i-C$_3$H$_7$— | O | CH$_3$ | m-CF$_3$ | H |
| 55 | i-C$_4$H$_9$— | O | CH$_3$ | m-CF$_3$ | H |

TABLE I-continued

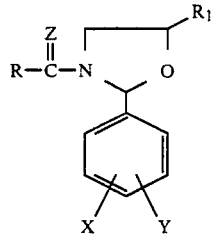

| Compound Number | R | Z | R₁ | X | Y |
|---|---|---|---|---|---|
| 56 | $C_3H_7-$ | O | $CH_3$ | $m-CF_3$ | H |
| 57 | $C_3H_7-$ | O | $CH_3$ | $m-CF_3$ | H |
| 58 | $2,4-Cl_2C_6H_3OCH_2-$ | O | $CH_3$ | $m-CF_3$ | H |
| 59 | $C_2H_5-$ | O | H | $m-CF_3$ | H |
| 60 | $C_2H_5NH-$ | O | H | $m-CF_3$ | H |
| 61 | $C_2H_5O-$ | O | H | $m-CF_3$ | H |
| 62 | $C_2H_5S-$ | O | H | $m-CF_3$ | H |
| 63 | $C_2H_5-$ | O | $C_2H_5$ | m-CN | H |
| 64 | $i-C_4H_9-$ | O | $C_2H_5$ | m-CN | H |
| 65 | $t-C_4H_9CH_2-$ | O | $C_2H_5$ | m-CN | H |
| 66 | $t-C_4H_9-$ | O | $C_2H_5$ | m-CN | H |
| 67 | $(CH_3)_2C=CH-$ | O | $C_2H_5$ | m-CN | H |
| 68 | $CH_3CH=CH-$ | O | $C_2H_5$ | m-CN | H |
| 69 | $CH_3OCH_2-$ | O | $C_2H_5$ | m-CN | H |
| 70 | $c-C_4H_7-$ | O | $C_2H_5$ | m-CN | H |
| 71 | $CH_2=C(CH_3)-$ | O | $C_2H_5$ | m-CN | H |
| 72 | $C_2H_5CH(CH_3)-$ | O | $C_2H_5$ | m-CN | H |
| 73 | cyclopentyl-$CH_2-$ | O | $C_2H_5$ | m-CN | H |
| 74 | $2,4-Cl_2C_6H_3OCH_2$ | O | $C_2H_5$ | m-CN | H |
| 75 | $c-C_6H_{11}CH_2-$ | O | $C_2H_5$ | m-CN | H |
| 76 | $i-C_3H_7-$ | O | $C_2H_5$ | m-Cl | H |
| 77 | $i-C_4H_9-$ | O | $C_2H_5$ | m-Cl | H |
| 78 | $t-C_4H_9-CH_2-$ | O | $C_2H_5$ | m-Cl | H |
| 78 | $(CH_3)_2C=CH-$ | O | $C_2H_5$ | m-Cl | H |
| 80 | $CH_3CH=CH-$ | O | $C_2H_5$ | m-Cl | H |
| 81 | $c-C_6H_{11}CH_2-$ | O | $C_2H_5$ | m-Cl | H |
| 82 | $i-C_4H_9-$ | O | $C_2H_5$ | m-Br | H |
| 83 | $t-C_4H_9CH_2-$ | O | $C_2H_5$ | m-Br | H |
| 84 | $(CH_3)_2C=CH-$ | O | $C_2H_5$ | m-Br | H |
| 85 | $CH_3CH=CH-$ | O | $C_2H_5$ | m-Br | H |
| 86 | $c-C_6H_{11}CH_2-$ | O | $C_2H_5$ | m-Br | H |
| 87 | $i-C_3H_7O-$ | O | $CH_3$ | m-Br | H |
| 88 | $i-C_4H_9-$ | O | $C_2H_5$ | $m-CF_3$ | p-Cl |
| 89 | $CH_3NH-$ | O | $C_2H_5$ | m-Cl | H |
| 90 | $C_6H_5NH-$ | O | $C_2H_5$ | m-Cl | H |
| 91 | $p-ClC_6H_5NH-$ | O | $C_2H_5$ | m-Cl | H |
| 92 | $m-ClC_6H_5NH-$ | O | $C_2H_5$ | m-Cl | H |
| 93 | $m-CF_3C_6H_5NH-$ | O | $C_2H_5$ | m-Cl | H |
| 94 | $p-NC-C_6H_5NH-$ | O | $C_2H_5$ | m-Cl | H |
| 95 | $m-CF_3C_6H_5NH-$ | O | $C_2H_5$ | $m-CF_3$ | H |
| 96 | $CH_3NH-$ | O | $C_2H_5$ | $m-CF_3$ | H |
| 97 | $C_6H_5NH-$ | O | $C_2H_5$ | $m-CF_3$ | H |
| 98 | $CH_3CH_2NH-$ | O | $C_2H_5$ | $m-CF_3$ | H |
| 99 | $m-ClC_6H_5NH-$ | O | $C_2H_5$ | $m-CF_3$ | H |
| 100 | $CH_3CH_2CH_2NH-$ | O | $C_2H_5$ | $m-CF_3$ | H |
| 101 | $CH_3CH_2CH_2CH_2NH-$ | O | $C_2H_5$ | $m-CF_3$ | H |
| 102 | $(CH_3)_2CHNH-$ | O | $C_2H_5$ | $m-CF_3$ | H |
| 103 | $CH_3CH_2NH-$ | O | $CH_3$ | $m-CF_3$ | H |
| 104 | $CH_3CH_2NH-$ | O | $C_2H_5$ | m-CN | H |
| 105 | $ClCH_2CH_2NH-$ | O | $C_2H_5$ | $m-CF_3$ | H |
| 106 | $CH_3CH_2CH_2NH-$ | O | $CH_3$ | $m-CF_3$ | H |
| 107 | $(CH_3)_2CHNH-$ | O | $CH_3$ | $m-CF_3$ | H |
| 108 | $CH_3CH_2CH_2NH-$ | O | $C_2H_5$ | m-Cl | H |
| 109 | $CH_3(CH_2)_5NH-$ | O | $C_2H_5$ | $m-CF_3$ | H |
| 110 | $CH_2=CHCH_2NH-$ | O | $C_2H_5$ | m-Br | H |
| 111 | $(CH_3)_2CHNH-$ | O | $C_2H_5$ | $m-CF_3$ | p-Cl |
| 112 | $C_6H_5CH_2NH-$ | O | $C_2H_5$ | $m-CF_3$ | H |
| 113 | $CH_2=CH-CH_2NH-$ | O | $C_2H_5$ | $m-CF_3$ | p-Cl |

TABLE I-continued

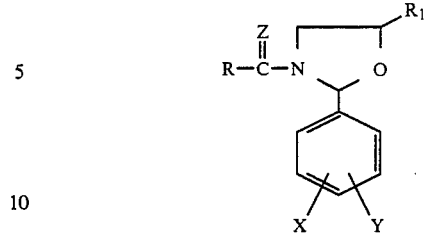

| Compound Number | R | Z | R₁ | X | Y |
|---|---|---|---|---|---|
| 114 | $CH_2=CH-CH_2NH-$ | O | $C_2H_5$ | $m-CF_3$ | H |

In the above table, a small "c" refers to a cyclo compound.

HERBICIDAL ACTIVITY TESTS

This example offers herbicidal activity test data to show the effectiveness of the compounds of the invention. The effect is observed by comparing the extent of weed control in test flats treated with the compounds against that occurring in similar control flats. The soil used in these tests was a sandy loam soil from the Livermore, Calif. area.

Also added to the soil was 17-17-17 fertilizer (N—P₂O₅—K₂O on a weight basis), amounting to 100 ppm by weight with respect to the soil and 200 ppm Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABR |
|---|---|---|
| GRASSES: | | |
| watergrass | Echinochloa crusgalli | WG |
| wild oat | Avena fatua | WO |
| green foxtail | Setaria viridis | FT |
| yellow nutsedge | Cyperus esculentus | YNS |
| Broadleaf Weeds: | | |
| annual morningglory | Ipomea purpurea | AMG |
| velvetleaf | Abutilon theoprasti | VL |
| curly dock | Rumex crispus | CD |

Sufficient seeds were planted to produce several seedlings per inch in each row. The flats were then placed in a greenhouse maintained at 70° to 85° F. (21° to 30° C.) and watered daily by sprinkler.

In pre-emergent testing (PES) the herbicie is incorporated into the soil prior to planting of the seeds.

In post-emergent testing (POST) chemical application is made by spraying 12 days after planting. The spray solution is prepared by dissolving 84 mg of herbicide compound in 20 ml of acetone containing 0.5% Tween ® 20 (polyoxyethylene sorbitan monolaurate), then adding 20 ml of water to the resulting solution. The solution is sprayed at 25 gallon/acre.

Approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in Table II below.

TABLE II

GREENHOUSE HERBICIDE TEST RESULTS

| Compound No. | Application Rate (lb/A) | Method | \multicolumn{8}{c}{Percent Injury} |
|---|---|---|---|---|---|---|---|---|---|---|

| Compound No. | Rate (lb/A) | Method | FT | WG | WO | AMG | VL | MD | CD | YNS |
|---|---|---|---|---|---|---|---|---|---|---|
| 1 | 4.00 | PES | 0 | 0 | 0 | 0 | 0 | 0 | 0 | 0 |
|   | 4.00 | POS | 0 | 0 | 0 | 0 | 0 | 0 | 0 | 0 |
| 2 | 4.00 | PES | 100 | 100 | 60 | 100 | 100 | 100 | 50 | 60 |
|   | 4.00 | POS | 85 | 85 | 60 | 85 | 65 | 95 | 15 | 35 |
| 3 | 4.00 | PES | 100 | 100 | 60 | 95 | 100 | 100 | 100 | 50 |
|   | 4.00 | POS | 100 | 95 | 95 | 85 | 75 | 95 | 60 | 50 |
| 4 | 4.00 | PES | 100 | 100 | 60 | 100 | 100 | 100 | 100 | 85 |
|   | 4.00 | POS | 70 | 70 | 75 | 85 | 70 | 85 | 40 | 35 |
| 5 | 4.00 | PES | 100 | 100 | 60 | 100 | 100 | 100 | 95 | 75 |
|   | 4.00 | POS | 80 | 65 | 60 | 70 | 50 | 80 | 30 | 30 |
| 6 | 4.00 | PES | 100 | 100 | 50 | 35 | 50 | 100 | 30 | 35 |
|   | 4.00 | POS | 40 | 35 | 25 | 60 | 40 | 50 | 40 | 10 |
| 7 | 4.00 | PES | 10 | 0 | 0 | 0 | 0 | 10 | 0 | 0 |
|   | 4.00 | POS | 20 | 25 | 0 | 40 | 25 | 50 | 100 | 0 |
| 8 | 4.00 | PES | 0 | 0 | 0 | 0 | 0 | 0 | 0 | 0 |
|   | 4.00 | POS | 0 | 0 | 0 | 0 | 35 | 20 | 0 | 0 |
| 9 | 4.00 | PES | 50 | 0 | 0 | 0 | 0 | 0 | 0 | 0 |
|   | 4.00 | POS | 0 | 35 | 0 | 35 | 25 | 85 | 0 | 0 |
| 10 | 4.00 | PES | 95 | 95 | 85 | 25 | 0 | 0 | 90 | 0 |
|    | 4.00 | POS | 25 | 15 | 0 | 50 | 50 | 100 | 0 | 0 |
| 11 | 4.00 | PES | 95 | 95 | 65 | 60 | 95 | 95 | 60 | 70 |
|    | 4.00 | POS | 60 | 70 | 35 | 75 | 75 | 70 | 60 | 60 |
| 12 | 4.00 | PES | 35 | 0 | 0 | 25 | 10 | 35 | 0 | 0 |
|    | 4.00 | POS | 0 | 30 | 0 | 40 | 0 | 35 | 0 | 0 |
| 13 | 4.00 | PES | 20 | 0 | 0 | 0 | 0 | 0 | 0 | 0 |
|    | 4.00 | POS | 20 | 25 | 0 | 60 | 0 | 35 | 0 | 0 |
| 14 | 4.00 | PES | 95 | 100 | 35 | 85 | 100 | 100 | 100 | 50 |
|    | 4.00 | POS | 80 | 60 | 25 | 60 | 35 | 50 | 20 | 25 |
| 15 | 4.00 | PES | 0 | 0 | 0 | 10 | 0 | 35 | 0 | 0 |
|    | 4.00 | POS | 20 | 25 | 0 | 0 | 0 | 35 | 0 | 0 |
| 16 | 4.00 | PES | 95 | 95 | 20 | 65 | 100 | 100 | 60 | 0 |
|    | 4.00 | POS | 60 | 60 | 25 | 75 | 25 | 50 | 80 | 10 |
| 17 | 4.00 | PES | 40 | 0 | 0 | 0 | 0 | 0 | 0 | 0 |
|    | 4.00 | POS | 0 | 20 | 0 | 20 | 0 | 50 | 0 | 0 |
| 18 | 4.00 | PES | 85 | 65 | 25 | 10 | 10 | 60 | 40 | 0 |
|    | 4.00 | POS | 35 | 25 | 10 | 25 | 35 | 40 | 25 | 10 |
| 19 | 4.00 | PES | 100 | 90 | 45 | 40 | 90 | 95 | 65 | 0 |
|    | 4.00 | POS | 85 | 50 | 40 | 40 | 40 | 50 | 35 | 25 |
| 20 | 4.00 | PES | 95 | 100 | 65 | 100 | 100 | 100 | 75 | 25 |
|    | 4.00 | POS | 65 | 60 | 35 | 60 | 50 | 80 | 50 | 10 |
| 21 | 4.00 | PES | 100 | 100 | 40 | 100 | 100 | 100 | 100 | 70 |
|    | 4.00 | POS | 85 | 75 | 40 | 50 | 50 | 80 | 70 | 50 |
| 22 | 4.00 | PES | 100 | 95 | 40 | 30 | 100 | 100 | 50 | 0 |
|    | 4.00 | POS | 80 | 60 | 30 | 40 | 35 | 50 | 40 | 10 |
| 23 | 4.00 | PES | 90 | 40 | 0 | 20 | 25 | 40 | 30 | 0 |
|    | 4.00 | POS | 30 | 15 | 10 | 50 | 35 | 50 | 30 | 10 |
| 24 | 4.00 | PES | 50 | 0 | 0 | 0 | 0 | 0 | 25 | 0 |
|    | 4.00 | POS | 0 | 0 | 0 | 15 | 15 | 25 | 10 | 0 |
| 25 | 4.00 | PES | 100 | 100 | 50 | 95 | 80 | 100 | 85 | 10 |
|    | 4.00 | POS | 50 | 60 | 50 | 60 | 70 | 60 | 40 | 25 |
| 26 | 4.00 | PES | 95 | 100 | 30 | 25 | 25 | 1000 | 25 | 0 |
|    | 4.00 | POS | 30 | 25 | 30 | 60 | 60 | 60 | 35 | 0 |
| 27 | 4.00 | PES | 0 | 0 | 0 | 0 | 0 | 0 | 0 | 0 |
|    | 4.00 | POS | 15 | 25 | 0 | 20 | 20 | 75 | 25 | 0 |
| 28 | 4.00 | PES | 35 | 0 | 0 | 20 | 0 | 20 | 20 | 0 |
|    | 4.00 | POS | 35 | 20 | 0 | 35 | 20 | 40 | 20 | 0 |
| 29 | 4.00 | PES | 50 | 75 | 75 | 0 | 0 | 0 | 0 | 0 |
|    | 4.00 | POS | 25 | 20 | 0 | 40 | 30 | 35 | 0 | 0 |
| 30 | 4.00 | PES | N | N | N | N | N | N | N | N |
|    | 4.00 | POS | 0 | 30 | 0 | 40 | 35 | 50 | N | 0 |
| 31 | 4.00 | PES | 80 | 80 | 40 | 75 | 100 | 100 | N | 0 |
|    | 4.00 | POS | 50 | 50 | 40 | 75 | 80 | 75 | N | 0 |
| 32 | 4.00 | PES | 100 | 100 | 70 | 100 | 100 | 100 | N | 15 |
|    | 4.00 | POS | 75 | 60 | 40 | 85 | 75 | 85 | N | 15 |
| 33 | 4.00 | PES | 85 | 80 | 30 | 100 | 100 | 100 | N | 0 |
|    | 4.00 | POS | 75 | 75 | 35 | 80 | 80 | 80 | N | 50 |
| 34 | 4.00 | PES | 95 | 100 | 60 | 100 | 100 | 100 | N | 60 |
|    | 4.00 | POS | 75 | 75 | 70 | 80 | 85 | 75 | N | N |
| 35 | 4.00 | PES | 60 | 80 | 0 | 80 | 95 | 100 | N | 0 |
|    | 4.00 | POS | 90 | 60 | 10 | 30 | 70 | 85 | N | 40 |
| 36 | 4.00 | PES | 10 | 50 | 90 | 5 | 0 |   | N | 0 |
|    | 4.00 | POS | 5 | 0 | 0 | 10 | 10 | 30 | N | 0 |
| 37 | 4.00 | PES | 100 | 100 | 70 | 90 | 100 | 100 | N | 10 |
|    | 4.00 | POS | 80 | 80 | 30 | 50 | 70 | 85 | N | 0 |
| 38 | 4.00 | PES | 100 | 100 | 90 | 95 | 100 | 100 | N | 30 |

TABLE II-continued

GREENHOUSE HERBICIDE TEST RESULTS

| Compound No. | Application Rate (lb/A) | Method | Percent Injury | | | | | | | |
|---|---|---|---|---|---|---|---|---|---|---|
| | | | FT | WG | WO | AMG | VL | MD | CD | YNS |
| | 4.00 | POS | 90 | 80 | 60 | 90 | 80 | 85 | N | 50 |
| 39 | 4.00 | PES | 70 | 30 | 90 | 0 | 5 | 20 | N | 0 |
| | 4.00 | POS | 10 | 0 | 0 | 20 | 10 | 70 | N | 0 |
| 40 | 4.00 | PES | 0 | 0 | 0 | 0 | 0 | 0 | N | 0 |
| | 4.00 | POS | 0 | 0 | 0 | 0 | 0 | 0 | N | 0 |
| 41 | 4.00 | PES | 40 | 75 | 35 | 10 | 40 | 90 | 25 | 25 |
| | 4.00 | POS | 25 | 35 | 0 | 35 | 40 | 70 | 20 | 0 |
| 42 | 4.00 | PES | 90 | 100 | 20 | 40 | 60 | 100 | N | 0 |
| | 4.00 | POS | 10 | 0 | 0 | 20 | 30 | 90 | N | 0 |
| 43 | 4.00 | PES | 0 | 0 | 0 | 0 | 0 | 0 | N | 0 |
| | 4.00 | POS | 30 | 10 | 0 | 0 | 10 | 10 | N | 0 |
| 44 | 4.00 | PES | 100 | 100 | 40 | 30 | 70 | 100 | N | 0 |
| | 4.00 | POS | 60 | 50 | 10 | 10 | 50 | 80 | N | 0 |
| 45 | 4.00 | PES | 50 | 0 | 0 | 0 | 0 | 0 | 0 | 0 |
| | 4.00 | POS | 0 | 0 | 0 | 25 | 35 | 85 | 15 | 0 |
| 46 | 4.00 | PES | 90 | 70 | 0 | 25 | 30 | 35 | 25 | 0 |
| | 4.00 | POS | 90 | 25 | 10 | 50 | 40 | 50 | 25 | 0 |
| 47 | 4.00 | PES | 20 | 0 | 0 | 0 | 0 | 0 | 0 | 0 |
| | 4.00 | POS | 0 | 0 | 0 | 10 | N | 10 | 0 | 0 |
| 48 | 4.00 | PES | 0 | 0 | 0 | 0 | 0 | 0 | 0 | 0 |
| | 4.00 | POS | 0 | 0 | 0 | 30 | 0 | 65 | | 0 |
| 49 | 4.00 | PES | 50 | 0 | 0 | 0 | 0 | 0 | 0 | 0 |
| | 4.00 | POS | 0 | 0 | 0 | 25 | 0 | 95 | 0 | 0 |
| 50 | 4.00 | PES | 85 | 65 | 20 | 20 | 20 | 20 | 20 | 0 |
| | 4.00 | POS | 10 | 10 | 10 | 40 | 35 | 50 | 20 | 0 |
| 51 | 4.00 | PES | 95 | 50 | 25 | 100 | 40 | 100 | N | 0 |
| | 4.00 | POS | 15 | 30 | 30 | 60 | 80 | 90 | N | 30 |
| 52 | 4.00 | PES | 5 | 0 | 0 | 5 | 10 | 10 | N | 30 |
| | 4.00 | POS | 10 | 0 | 5 | 100 | 90 | 95 | N | 0 |
| 53 | 4.00 | PES | 95 | 100 | 30 | 100 | 100 | 100 | 80 | 40 |
| | 4.00 | POS | 35 | 40 | 0 | 70 | 35 | 65 | 20 | 0 |
| 54 | 4.00 | PES | 20 | 0 | 0 | 0 | 0 | 10 | 0 | 0 |
| | 4.00 | POS | 0 | 15 | 0 | 20 | 10 | 35 | 0 | 0 |
| 55 | 4.00 | PES | 100 | 100 | 90 | 100 | 100 | 100 | 85 | 80 |
| | 4.00 | POS | 65 | 65 | 60 | 50 | 35 | 70 | 30 | 35 |
| 56 | 4.00 | PES | 95 | 90 | 50 | 100 | 100 | 95 | 60 | 80 |
| | 4.00 | POS | 60 | 75 | 60 | 50 | 50 | 50 | 60 | N |
| 57 | 4.00 | PES | 0 | 0 | 0 | 0 | 0 | 0 | N | 0 |
| | 4.00 | POS | 0 | 0 | 0 | 0 | 0 | 15 | N | 0 |
| 58 | 4.00 | PES | 5 | 0 | 0 | 0 | 0 | 10 | N | 0 |
| | 4.00 | POS | 10 | 0 | 5 | 100 | 80 | 95 | N | 0 |
| 59 | 4.00 | PES | 10 | 20 | 0 | 65 | 15 | 10 | 10 | 0 |
| | 4.00 | POS | 10 | 10 | 0 | 35 | 25 | 50 | 20 | 0 |
| 60 | 4.00 | PES | 20 | 25 | 0 | 0 | 0 | 20 | 0 | 0 |
| | 4.00 | POS | 10 | 10 | 10 | 35 | 35 | 70 | 0 | 0 |
| 61 | 4.00 | PES | 10 | 15 | 0 | 0 | 0 | 0 | 0 | 0 |
| | 4.00 | POS | 0 | 0 | 0 | 0 | 0 | 0 | 0 | 0 |
| 62 | 4.00 | PES | 40 | 50 | 0 | 10 | 20 | 15 | 0 | 0 |
| | 4.00 | POS | 50 | 50 | 0 | 100 | 100 | 40 | 20 | 0 |
| 63 | 4.00 | PES | 85 | 95 | 10 | 75 | 25 | 50 | 60 | 50 |
| | 4.00 | POS | 25 | 15 | 10 | 35 | 35 | 40 | 50 | 20 |
| 64 | 4.00 | PES | 10 | 20 | 5 | 40 | 50 | 30 | N | 10 |
| | 4.00 | POS | 100 | 100 | 20 | 95 | 100 | 100 | N | 70 |
| 65 | 4.00 | PES | 0 | 0 | 0 | 20 | 30 | 30 | N | 0 |
| | 4.00 | POS | 60 | 85 | 100 | 20 | 20 | 95 | N | 0 |
| 66 | 4.00 | PES | 10 | 0 | 0 | 20 | 20 | 35 | 35 | 10 |
| | 4.00 | POS | 10 | 50 | 10 | 40 | 65 | 75 | 50 | 0 |
| 67 | 4.00 | PES | 100 | 90 | 20 | 50 | 65 | 90 | 50 | 60 |
| | 4.00 | POS | 100 | 100 | 40 | 35 | 100 | 100 | 90 | 75 |
| 68 | 4.00 | PES | 0 | 5 | 0 | 40 | 40 | 30 | N | 0 |
| | 4.00 | POS | 100 | 100 | 50 | 90 | 95 | 100 | N | 60 |
| 69 | 4.00 | PES | 5 | 5 | 0 | 10 | 20 | 20 | N | 0 |
| | 4.00 | POS | 0 | 0 | 0 | 40 | 40 | 40 | N | 0 |
| 70 | 4.00 | PES | 10 | 30 | 0 | 0 | 0 | 10 | N | 0 |
| | 4.00 | POS | 0 | 10 | 0 | 0 | 20 | 30 | N | 70 |
| 71 | 4.00 | PES | 0 | 0 | 0 | 0 | 0 | 5 | N | 0 |
| | 4.00 | POS | 0 | 0 | 0 | 5 | 5 | 20 | N | 0 |
| 72 | 4.00 | PES | 0 | 0 | 0 | 0 | 0 | 0 | N | 0 |
| | 4.00 | POS | 0 | 0 | 0 | 0 | 0 | 0 | N | 0 |
| 73 | 4.00 | PES | 90 | 5 | 90 | 10 | 20 | 100 | N | 20 |
| | 4.00 | POS | 30 | 40 | 0 | 20 | 30 | 80 | N | 0 |
| 74 | 4.00 | PES | 0 | 0 | 0 | 0 | 0 | 0 | N | 0 |
| | 4.00 | POS | 0 | 0 | 0 | 30 | 30 | 90 | N | 0 |
| 75 | 4.00 | PES | 0 | 0 | 0 | 10 | 10 | 50 | N | 0 |
| | 4.00 | POS | 0 | 0 | 0 | 10 | 10 | 20 | N | 0 |
| 76 | 4.00 | PES | 0 | 0 | 0 | 0 | 0 | 0 | 0 | 0 |
| | 4.00 | POS | 15 | 15 | 0 | 25 | 20 | 35 | 35 | 0 |
| 77 | 4.00 | PES | 95 | 90 | 40 | 50 | 70 | 70 | 50 | 50 |

TABLE II-continued

GREENHOUSE HERBICIDE TEST RESULTS

| Compound No. | Application Rate (lb/A) | Method | Percent Injury | | | | | | | |
|---|---|---|---|---|---|---|---|---|---|---|
| | | | FT | WG | WO | AMG | VL | MD | CD | YNS |
| | 4.00 | POS | 100 | 75 | 35 | 50 | 50 | 70 | 50 | 40 |
| 78 | 4.00 | PES | 5 | 5 | 0 | 20 | 40 | 30 | N | 0 |
| | 4.00 | POS | 100 | 50 | 10 | 10 | 0 | 80 | N | 0 |
| 79 | 4.00 | PES | 0 | 10 | 0 | 30 | 40 | 30 | N | 0 |
| | 4.00 | POS | 100 | 100 | 10 | 30 | 75 | 100 | N | 0 |
| 80 | 4.00 | PES | 0 | 20 | 0 | 20 | 30 | 40 | N | 0 |
| | 4.00 | POS | 100 | 100 | 0 | 20 | 20 | 100 | N | 0 |
| 81 | 4.00 | PES | 100 | 50 | 0 | 10 | 60 | 90 | N | 5 |
| | 4.00 | POS | 0 | 0 | 0 | 20 | 30 | 40 | N | 0 |
| 82 | 4.00 | PES | 100 | 100 | 40 | 40 | 100 | 100 | 80 | 35 |
| | 4.00 | POS | 60 | 60 | 60 | 75 | 60 | 75 | 40 | 50 |
| 83 | 4.00 | PES | 100 | 100 | 25 | 20 | 0 | 90 | 20 | 0 |
| | 4.00 | POS | 40 | 50 | 25 | 60 | 70 | 70 | 0 | 0 |
| 84 | 4.00 | PES | 40 | 50 | 20 | 40 | 40 | 70 | 30 | 0 |
| | 4.00 | POS | 100 | 100 | 20 | 20 | 40 | 100 | 100 | 0 |
| 85 | 4.00 | PES | 65 | 65 | 25 | 60 | 95 | 100 | N | 0 |
| | 4.00 | POS | 85 | 70 | 40 | 75 | 65 | 90 | N | 0 |
| 86 | 4.00 | PES | 0 | 0 | 0 | 25 | 0 | 25 | N | 0 |
| | 4.00 | POS | 15 | 0 | 0 | 30 | 40 | 50 | N | 0 |
| 87 | 4.00 | PES | 95 | 80 | 90 | 40 | 10 | 10 | N | 0 |
| | 4.00 | POS | 30 | 10 | 10 | 50 | 40 | 90 | N | 0 |
| 88 | 4.00 | PES | 100 | 100 | 75 | 75 | 100 | 100 | N | 0 |
| | 4.00 | POS | 100 | 70 | 80 | 85 | 85 | 100 | N | 40 |
| 89 | 4.00 | PES | 30 | 0 | 0 | 0 | 0 | 60 | 0 | 0 |
| | 4.00 | POS | 0 | 0 | 0 | 10 | 0 | 15 | 5 | 0 |
| 90 | 4.00 | PES | 40 | 0 | 0 | 0 | 0 | 50 | 0 | 0 |
| | 4.00 | POS | 0 | 0 | 0 | 10 | 0 | 20 | 10 | 0 |
| 91 | 4.00 | PES | 0 | 0 | 0 | 0 | 0 | 0 | 0 | 0 |
| | 4.00 | POS | 0 | 0 | 0 | 0 | 0 | 20 | 0 | 0 |
| 92 | 4.00 | PES | 0 | 0 | 0 | 0 | 0 | 0 | 0 | 0 |
| | 4.00 | POS | 0 | 0 | 0 | 0 | 0 | 100 | 0 | 0 |
| 93 | 4.00 | PES | 0 | 0 | 0 | 5 | 0 | 100 | 20 | 0 |
| | 4.00 | POS | 0 | 0 | 0 | 15 | 40 | 100 | 10 | 0 |
| 94 | 4.00 | PES | 0 | 0 | 0 | 0 | 0 | 90 | 0 | 0 |
| | 4.00 | POS | 0 | 0 | 0 | 0 | 20 | 25 | 0 | 0 |
| 95 | 4.00 | PES | 0 | 0 | 0 | 0 | 0 | 20 | 90 | 0 |
| | 4.00 | POS | 0 | 0 | 0 | 25 | 20 | 60 | 90 | 0 |
| 96 | 4.00 | PES | 100 | 90 | 20 | 80 | 40 | 90 | 90 | 25 |
| | 4.00 | POS | 90 | 60 | 0 | 75 | 75 | 90 | 50 | 0 |
| 97 | 4.00 | PES | 100 | 70 | 50 | 25 | 40 | 90 | 100 | 0 |
| | 4.00 | POS | 95 | 35 | 25 | 90 | 40 | 90 | 85 | 0 |
| 98 | 4.00 | PES | 100 | 100 | 60 | 100 | 95 | 100 | 100 | 0 |
| | 4.00 | POS | 90 | 60 | 35 | 90 | 20 | 80 | 80 | 0 |
| 99 | 4.00 | PES | 0 | 0 | 0 | 0 | 25 | 40 | 80 | 0 |
| | 4.00 | POS | 0 | 0 | 0 | 35 | 80 | 90 | 0 | 0 |
| 100 | 4.00 | PES | 100 | 100 | 40 | 100 | 100 | 100 | 100 | 35 |
| | 4.00 | POS | 100 | 100 | 95 | 75 | 60 | 100 | 100 | 35 |
| 101 | 4.00 | PES | 90 | 85 | 0 | 75 | 100 | 100 | 90 | 0 |
| | 4.00 | POS | 100 | 90 | 40 | 75 | 60 | 100 | 90 | 0 |
| 102 | 4.00 | PES | 100 | 95 | 40 | 100 | 95 | 90 | 100 | 40 |
| | 4.00 | POS | 100 | 90 | 100 | 75 | 70 | 100 | 100 | 10 |
| 103 | 4.00 | PES | 100 | 100 | 60 | 100 | 100 | 100 | 60 | N |
| | 4.00 | POS | 85 | 65 | 50 | 65 | 40 | 60 | 25 | 0 |
| 104 | 4.00 | PES | 100 | 90 | 40 | 85 | 100 | 100 | 100 | 0 |
| | 4.00 | POS | 90 | 75 | 60 | 70 | 75 | 85 | 100 | 20 |
| 105 | 4.00 | PES | 85 | 85 | 25 | 20 | 50 | 85 | 50 | 0 |
| | 4.00 | POS | 70 | 75 | 40 | 60 | 50 | 70 | 60 | 10 |
| 106 | 4.00 | PES | 90 | 90 | 50 | 90 | 100 | 100 | 65 | N |
| | 4.00 | POS | 80 | 75 | 65 | 50 | 50 | 100 | 50 | N |
| 107 | 4.00 | PES | 90 | 90 | 65 | 100 | 100 | 100 | 60 | 0 |
| | 4.00 | POS | 100 | 75 | 60 | 60 | 50 | 70 | 60 | N |
| 108 | 4.00 | PES | 90 | 95 | 30 | 20 | 20 | 75 | 95 | 0 |
| | 4.00 | POS | 30 | 30 | 15 | 65 | 35 | 65 | 20 | 0 |
| 109 | 4.00 | PES | 80 | 25 | 0 | 20 | 0 | 50 | 20 | 0 |
| | 4.00 | POS | 20 | 20 | 0 | 35 | 35 | 90 | 65 | 0 |
| 110 | 4.00 | PES | 95 | 50 | 20 | 35 | 0 | 100 | 35 | 0 |
| | 4.00 | POS | 30 | 25 | 10 | 50 | 10 | 75 | 20 | 0 |
| 111 | 4.00 | PES | 100 | 100 | 65 | 50 | N | 100 | 100 | 0 |
| | 4.00 | POS | 95 | 65 | 90 | 65 | N | 65 | 95 | 0 |
| 112 | 4.00 | PES | 100 | 85 | 5 | 50 | 100 | 100 | N | N |
| | 4.00 | POS | 10 | 50 | 0 | 20 | 50 | 80 | N | 0 |
| 113 | 4.00 | PES | 90 | 95 | 35 | 50 | 70 | 100 | N | 0 |
| | 4.00 | POS | 100 | 60 | 50 | 70 | 75 | 100 | N | 0 |
| 114 | 4.00 | PES | 100 | 100 | 50 | 100 | 100 | 100 | N | 0 |
| | 4.00 | POS | 85 | 75 | 60 | 75 | 75 | 85 | N | 0 |

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. Dusts

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. Emulsifiable Concentrates

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and nonwater-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. Granules and Pellets

Granules and pellets are physically stable, particulate composicompositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. Microcapsules

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. In General

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Post-emergent application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. An oxazolidine having the formula

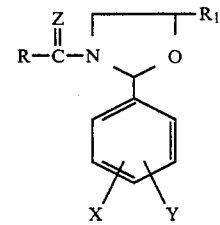

wherein
R is selected from the group consisting of alkyl having from 1 to about 8 carbon atoms, substituted alkyl wherein the alkyl group has from 1 to about 8 carbon atoms and the substituent is selected from the group consisting of halogen or trifluoromethyl, alkenyl having from 2 to about 5 carbon atoms, cycloalkyl in which the cyclo ring has from 3 to about 6 carbon atoms and the alkyl group has from 1 to about 3 carbon atoms, benzyl, alkoxyalkyl wherein the alkoxy group has from 1 to about 2 carbon atoms and the alkyl group has from 1 to about 2 carbon atoms, carboalkoxyalkyl wherein the alkoxy group has from 1 to about 2 carbon atoms and the alkyl group has from 1 to about 5 carbon atoms, alkylthioalkyl wherein the alkylthio group has from 1 to about 3 carbon atoms and the alkyl group has from 1 to about 3 carbon atoms, phenyl, substituted phenyl wherein the substituent is selected from the group consisting of halogen or trifluoromethyl, furanyl, phenoxyalkyl wherein the alkyl group has from about 1 to about 2 carbon atoms, carboalkoxy wherein the alkoxy group has from 1 to about 3 carbon atoms, substituted phenoxyalkyl wherein the alkyl group has from 1 to about 2 carbon atoms and the substituent is selected from the group consisting of halogen and trifluoromethyl, alkylamino wherein the alkyl group has from 1 to about 6 carbon atoms, alkoxy having from from 1 to about 5 carbon atoms, chloroethylamino, alkylthio wherein the alkyl group has from 1 to about 5 carbon atoms, cycloalkylalkyl wherein the cyclo ring has from 3 to about 6 carbon atoms and each alkyl group has from 1 to about 3 carbon atoms, cycloalkenylalkyl wherein the cyclo ring has from 5 to about 6 carbon atoms and each alkyl group has from 1 to about 3 carbon atoms, phenylamino, substituted phenylamino wherein the substituent is selected from the group consisting of halogen, trifluoromethyl or cyano, alkenylamino wherein the alkyl group has from 2 to about 5 carbon atoms, and benzylamino;

Z is oxygen;

$R_1$ is selected from the group consisting of alkyl or halo-substituted alkyl wherein the alkyl group has from 1 to 4 carbon atoms; and X is selected from the group consisting of trifluoromethyl, cyano, thioalkyl, halothioalkyl and sulfonylalkyl, wherein the alkyl groups in each alkyl-containing moiety have from 1 to 4 carbon atoms and Y is hydrogen or chlorine.

2. A compound according to claim 1 wherein $R_1$ is ethyl.

3. A compound according to claim 1 wherein X is trifluoromethyl and Y is halogen.

4. A compound according to claim 1 wherein Z is oxygen.

5. A compound according to claim 1 wherein $R_1$ is ethyl, X is trifluoromethyl, Y is hydrogen, Z is oxygen and R is isopropyl.

6. A compound according to claim 1 wherein $R_1$ is ethyl, X is trifluoromethyl, Y is hydrogen, Z is oxygen and R is isobutyl.

7. A compound according to claim 1 wherein $R_1$ is ethyl, X is trifluoromethyl, Y is hydrogen, Z is oxygen and R is 3-methylcrotyl.

8. A compound according to claim 1 wherein $R_1$ is ethyl, X is trifluoromethyl, Y is hydrogen, Z is oxygen and R is crotyl.

9. A compound according to claim 1 wherein $R_1$ is ethyl, X is trifluoromethyl, Y is hydrogen, Z is oxygen and R is 3-trifluoromethylbutyl.

10. A compound according to claim 1 wherein $R_1$ is ethyl, X is trifluoromethyl and Z is oxygen.

11. An herbicidal composition comprising an oxazolidine compound having the formula

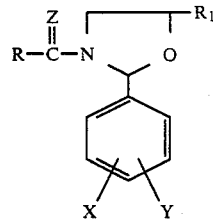

wherein

R is selected from the group consisting of alkyl having from 1 to about 8 carbon atoms, substituted alkyl wherein the alkyl group has from 1 to about 8 carbon atoms and the substituent is selected from the group consisting of halogen or trifluoromethyl, alkenyl having from 2 to about 5 carbon atoms, cycloalkyl in which the cyclo ring has from 3 to about 6 carbon atoms and the alkyl group has from 1 to about 3 carbon atoms, benzyl, alkoxyalkyl wherein the alkoxy group has from 1 to about 2 carbon atoms and the alkyl group has from 1 to about 2 carbon atoms, carboalkoxyalkyl wherein the alkoxy group has from 1 to about 2 carbon atoms and the alkyl group has from 1 to about 5 carbon atoms, alkylthioalkyl wherein the alkylthio group has from 1 to about 3 carbon atoms and the alkyl group has from 1 to about 3 carbon atoms, phenyl, substituted phenyl wherein the substituent is selected from the group consisting of halogen or trifluoromethyl, furanyl, phenoxyalkyl wherein the alkyl group has from about 1 to about 2 carbon atoms, carboalkoxy wherein the alkoxy group has from 1 to about 3 carbon atoms, substituted phenoxyalkyl wherein the alkyl group has from 1 to about 2 carbon atoms and the substituent is selected from the group consisting of halogen and trifluoromethyl, alkylamino wherein the alkyl group has from 1 to about 6 carbon atoms, alkoxy having from from 1 to about 5 carbon atoms, chloroethylamino, alkylthio wherein the alkyl group has from 1 to about 5 carbon atoms, cycloalkylalkyl wherein the cyclo ring has from 3 to about 6 carbon atoms and each alkyl group has from 1 to about 3 carbon atoms, cycloalkenylalkyl wherein the cyclo ring has from 5 to about 6 carbon atoms and each alkyl group has from 1 to about 3 carbon atoms, phenylamino, substituted phenylamino wherein the substituent is selected from the group consisting of halogen, trifluoromethyl or cyano, alkenylamino wherein the alkyl group has from 2 to about 5 carbon atoms, and benzylamino;

Z is oxygen;

$R_1$ is selected from the group consisting of alkyl or halo-substituted alkyl wherein the alkyl group has from 1 to 4 carbon atoms; and X is selected from the group consisting of trifluoromethyl, cyano, thioalkyl, halothioalkyl, and sulfonylalkyl, wherein the alkyl groups in each alkyl-containing moiety have from 1 to 4 carbon atoms and Y is hydrogen or chlorine.

12. A composition according to claim 11 wherein $R_1$ is ethyl.

13. A composition according to claim 11 wherein X is trifluoromethyl and Y is hydrogen.

14. A composition according to claim 11 wherein Z is oxygen.

15. A composition according to claim 11 wherein $R_1$ is ethyl, X is trifluoromethyl, Y is hydrogen, Z is oxygen and R is isopropyl.

16. A composition according to claim 11 wherein $R_1$ is ethyl, X is trifluoromethyl, Y is hydrogen, Z is oxygen and R is isobutyl.

17. A composition according to claim 11 wherein $R_1$ is ethyl, X is trifluoromethyl, Y is hydrogen, Z is oxygen and R is 3-methylcrotyl.

18. A composition according to claim 11 wherein $R_1$ is ethyl, X is trifluoromethyl, Y is hydrogen, Z is oxygen and R is crotyl.

19. A composition according to claim 11 wherein $R_1$ is ethyl, X is trifluoromethyl, Y is hydrogen, Z is oxygen and R is 3-trifluoromethylbutyl.

20. A composition according to claim 11 wherein $R_1$ is ethyl, X is trifluoromethyl and Z is oxygen.

21. A method for controlling undesirable weed pests which comprises applying to the locus where control is desired a herbicidally effective amount of an oxazolidine compound having the formula

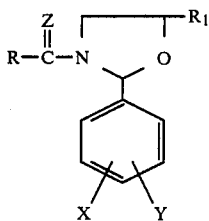

wherein
R is selected from the group consisting of alkyl having from 1 to about 8 carbon atoms, substituted alkyl wherein the alkyl group has from 1 to about 8 carbon atoms and the substituent is selected from the group consisting of halogen or trifluoromethyl, alkenyl having from 2 to about 5 carbon atoms, cycloalkyl in which the cyclo ring has from 3 to about 6 carbon atoms and the alkyl group has from 1 to about 3 carbon atoms, benzyl, alkoxyalkyl wherein the alkoxy group has from 1 to about 2 carbon atoms and the alkyl group has from 1 to about 2 carbon atoms, carboalkoxyalkyl wherein the alkoxy group has from 1 to about 2 carbon atoms and the alkyl group has from 1 to about 5 carbon atoms, alkylthioalkyl wherein the alkylthio group has from 1 to about 3 carbon atoms and the alkyl group has from 1 to about 3 carbon atoms, phenyl, substituted phenyl wherein the substituent is selected from the group consisting of halogen or trifluoromethyl, furanyl, phenoxyalkyl wherein the alkyl group has from about 1 to about 2 carbon atoms, carboalkoxy wherein the alkoxy group has from 1 to about 3 carbon atoms, substituted phenoxyalkyl wherein the alkyl group has from 1 to about 2 carbon atoms and the substituent is selected from the group consisting of halogen and trifluoromethyl, alkylamino wherein the alkyl group has from 1 to about 6 carbon atoms, alkoxy having from from 1 to about 5 carbon atoms, chloroethylamino, alkylthio wherein the alkyl group has from 1 to about 5 carbon atoms, cycloalkylalkyl wherein the cyclo ring has from 3 to about 6 carbon atoms and each alkyl group has from 1 to about 3 carbon atoms, cycloalkenylalkyl wherein the cyclo ring has from 5 to about 6 carbon atoms and each alkyl group has from 1 to about 3 carbon atoms, phenylamino, substituted phenylamino wherein the substituent is selected from the group consisting of halogen, trifluoromethyl or cyano, alkenylamino wherein the alkyl group has from 2 to about 5 carbon atoms, and benzylamino;

Z is oxygen;

$R_1$ is selected from the group consisting of alkyl or halo-substituted alkyl wherein the alkyl group has from 1 to 4 carbon atoms;

X is selected from the group consisting of trifluoromethyl and cyano,; and

Y is hydrogen or chlorine.

22. A method according to claim 21 wherein $R_1$ is ethyl.

23. A method according to claim 21 wherein X is trifluoromethyl and Y is hydrogen.

24. A method according to claim 21 wherein Z is oxygen.

25. A method according to claim 21 wherein $R_1$ is ethyl, X is trifluoromethyl, Y is hydrogen, Z is oxygen and R is isopropyl.

26. A method according to claim 21 wherein $R_1$ is ethyl, X is trifluoromethyl, Y is hydrogen, Z is oxygen and R is isobutyl.

27. A method according to claim 21 wherein $R_1$ is ethyl, X is trifluoromethyl, Y is hydrogen, Z is oxygen and R is 3-methylcrotyl.

28. A method according to claim 21 wherein $R_1$ is ethyl, X is trifluoromethyl, Y is hydrogen, Z is oxygen and R is crotyl.

29. A method according to claim 21 wherein $R_1$ is ethyl, X is trifluoromethyl, Y is hydrogen, Z is oxygen and R is 3-trifluoromethylbutyl.

30. A method according to claim 21 wherein $R_1$ is ethyl, X is trifluoromethyl and Z is oxygen.

* * * * *